United States Patent
Feuilloley

(10) Patent No.: US 7,763,194 B2
(45) Date of Patent: Jul. 27, 2010

(54) METHOD FOR CAPACITIVE MEASUREMENT OF ONE CHARACTERISTIC OF A THERMOPLASTIC CONTAINER IN A MOLD, AND MOLD EQUIPPED WITH SAME

(75) Inventor: Guy Feuilloley, Octeville sur Mer (FR)

(73) Assignee: Sidel Participations, Octeville sur Mer (FR)

( * ) Notice: Subject to any disclaimer, the term of this patent is extended or adjusted under 35 U.S.C. 154(b) by 565 days.

(21) Appl. No.: 11/665,769

(22) PCT Filed: Oct. 18, 2005

(86) PCT No.: PCT/FR2005/002585

§ 371 (c)(1),
(2), (4) Date: Apr. 19, 2007

(87) PCT Pub. No.: WO2006/042960

PCT Pub. Date: Apr. 27, 2006

(65) Prior Publication Data

US 2007/0290388 A1    Dec. 20, 2007

(30) Foreign Application Priority Data

Oct. 21, 2004    (FR) .................................. 04 11220

(51) Int. Cl.
*B29C 49/78* (2006.01)
(52) U.S. Cl. ..................... 264/40.1; 264/523; 425/140; 425/141; 425/540; 425/522

(58) Field of Classification Search .................. None
See application file for complete search history.

(56) References Cited

U.S. PATENT DOCUMENTS

| 2,616,068 | A |   | 10/1952 | McDonald |
|---|---|---|---|---|
| 5,175,428 | A | * | 12/1992 | Agerskov et al. ........ 250/223 B |
| 5,291,271 | A | * | 3/1994 | Juvinall et al. .............. 356/632 |
| 5,591,462 | A | * | 1/1997 | Darling et al. .............. 425/173 |
| 5,844,677 | A | * | 12/1998 | Dimmick et al. ......... 356/240.1 |
| 5,874,141 | A | * | 2/1999 | Matsui ...................... 428/36.9 |
| 6,285,451 | B1 | * | 9/2001 | Herron ....................... 356/630 |
| 6,584,805 | B1 | * | 7/2003 | Burns et al. ................ 65/29.12 |
| 6,620,352 | B1 | * | 9/2003 | Davis et al. ................. 264/40.4 |
| 6,806,459 | B1 | * | 10/2004 | Ringlien et al. ......... 250/223 B |
| 6,863,860 | B1 | * | 3/2005 | Birckbichler et al. ....... 264/410 |
| 6,985,221 | B2 | * | 1/2006 | Semersky et al. ........ 356/239.6 |
| 7,480,040 | B2 | * | 1/2009 | Juvinall et al. ........... 356/239.4 |
| 2003/0020193 | A1 | * | 1/2003 | Hamamoto et al. ........ 264/40.1 |

FOREIGN PATENT DOCUMENTS

| EP | 0 491 545 A | 6/1992 |
|---|---|---|
| EP | 0 544 022 A | 6/1993 |
| EP | 1 175 990 A | 1/2002 |
| JP | 08 025464 A | 1/1996 |

* cited by examiner

*Primary Examiner*—Monica A Huson
(74) *Attorney, Agent, or Firm*—Sughrue Mion, PLLC

(57) ABSTRACT

The invention concerns the manufacture of containers, in particular bottles, from thermoplastic material blanks, in particular PET, whereby a mold is used including at least one capacitive sensor inserted in its wall defining the molding cavity, the front side of the capacitive sensor being flush with the molding surface of the molding cavity and being configured in the continuity of the surface.

27 Claims, 3 Drawing Sheets

METHOD FOR CAPACITIVE MEASUREMENT OF ONE CHARACTERISTIC OF A THERMOPLASTIC CONTAINER IN A MOLD, AND MOLD EQUIPPED WITH SAME

FIELD OF THE INVENTION

The present invention relates to improvements made in the field of the manufacture of containers, particularly bottles, of thermoplastic, such as PET using a process involving the blow-molding or stretch-blow-molding of parisons, particularly of preforms.

DESCRIPTION OF THE PRIOR ART

Thermoplastic containers have predetermined physical characteristics which are dependent on the conditions in which the manufacturing process is run. Any drift in the manufacturing parameters may lead to a modification of these physical characteristics liable ultimately to lead to containers that cannot be used.

In particular, thermoplastic containers have wall thicknesses which differ according to the region of the container (body, shoulder, bottom in particular), these differences being determined in such a way that each of the regions has appropriate mechanical strength while at the same time contriving for these thicknesses to be minimized in order to economize on the amount of raw materials used.

However, the operating conditions of the installation may change during manufacture for various reasons and one or more parameters of the molding process may experience drifts which means that containers thus obtained have a wall thickness locally or in their entirety that does not meet the specification, in other words, containers in which at least certain wall regions are too thick and/or other regions are too thin, other regions yet perhaps being of the correct thickness. Such non-compliance is unacceptable: the wall is weakened in the regions where it is too thin; furthermore, the amount of material in the preforms is optimized so that the thickness profile of the molded container meets the specification which means that if certain regions of the molded container are too thick, this is in fact because material which should have been in one or more nearby regions has contributed to the formation of the excessively thick regions, which is therefore to the detriment of said nearby regions which for their part are therefore thinner than they should have been and are therefore weakened.

Likewise, the density, which is representative of the degree of crystallinity of the material of which the container is made, governs the ability of the container, without appreciable deformation, to withstand thermal stresses (pasteurization, hot-filling) or pressure stresses (carbonated liquids). Any drift in the density, and therefore in the degree of crystallinity, under the influence of modification(s) to the parameters of the molding process may lead to containers that are unable to withstand the anticipated stresses.

Checks may admittedly be made on the finished containers. However, in order to check the thickness, this currently requires checks performed using systems looking at containers traveling often at high speed. Now, these checks are performed in a region near the exit from the machine and require apparatus capable of following the output rate of the machine (typically several tens of thousands of containers per hour, with the Applicant Company's machines): apparatus that is sufficiently quick and accurate to detect extremely small drifts on the measured characteristics at such rates are not currently known.

Fuller checks are also possible but these then entail checks carried out on containers sampled at random during production and the results are obtained at a later time when a great many defective containers may have already been produced.

Added to these considerations is the fact that the absence of effective means of performing on-line real-time checks on the conformity of the manufactured products, and particularly their wall thickness, leads to the provision of a margin of safety in the predetermining of the wall thickness of the containers. This means that, for each container, the amount of raw material used exceeds the bare minimum necessary. Given the ever increasing cost of raw materials such as PET, at least in certain parts of the world, it would seem desirable to be able to gain better control over the individual amounts of raw material used and therefore in particular to have better checks on the thickness of the manufactured containers.

BRIEF DESCRIPTION OF THE INVENTION

The invention aims to provide a solution to the problem posed and to propose means giving the possibility of performing an effective check on at least one characteristic of each container manufactured so that any drift in this characteristic can be detected instantly or very quickly and operation of the molding installation can be adapted accordingly without delay so as to minimize the number of non-compliant containers.

To these ends, according to a first of its aspects, the invention proposes a method for measuring at least one physical characteristic of containers, particularly of bottles, manufactured by blow-molding or stretch-blow-molding of parisons made of thermoplastic, particularly of PET, in a mold comprising at least one molding cavity, characterized in that said measurement is made by detecting a capacitive effect or a variation in capacitive effect in the mold during blow-molding or stretch-blow-molding.

The method of the invention may find a particularly preferred application in checking the wall thickness of the container at least at one location thereon, or alternatively for checking the density of the material of the wall of the container at least at one location thereon (it being remembered that the density is representative of the degree of crystallinity of the material).

In a practical way in order to obtain optimum precision on the measurement, provision is made for the measurement to be made between the end of blow-molding or stretch-blow-molding and the start of mold opening while the wall of the container is in close contact with the molding surface of the molding cavity.

Thus, the invention makes it possible to get around the limitations due to the machine output rates, as mentioned hereinabove: specifically, by taking the measurement in the mold there is sufficient time available to take the measurement. As a concrete example, in order to measure the thickness of the wall of the container, implementing the method according to the invention gives a space of time of the order of 5 to 10 times that available when resorting to a visual checking system.

According to a second of its aspects, the invention proposes a mold for the manufacture of containers, particularly bottles, from parisons made of thermoplastic, particularly of PET, which mold, being arranged according to the invention for implementing the abovementioned measurement method, comprises at least one capacitive sensor inserted in its wall defining the molding cavity, the front face of the sensor lying flush with the surface of the cavity and being shaped as a continuation of the shape of said surface.

In a preferred embodiment, the capacitive sensor comprises a front face on which there are a central electrode and an external electrode which are separated by an annular intermediate region of dielectric material, said external electrode being in electrically conducting contact with the mold which forms the electrical ground. Given the weakness of the output signals from the sensor which are difficult to detect in a somewhat unfavorable electromagnetic environment, provision may advantageously be made for the sensor further to comprise an intermediate electrode (field electrode) interposed between the central electrode and the external electrode; advantageously, this intermediate electrode (field electrode) is connected in such a way as to be at a different potential than the central and external electrodes between which it is interposed.

In order to obtain optimum capacitive-sensor efficiency, it is desirable for it to be housed and fixed in a bore in the wall of the mold which runs approximately perpendicular to the surface of the molding cavity when this surface is flat or to the plane tangential to the surface of the molding cavity when this surface is curved.

In one advantageous embodiment that allows reliable checking of the wall thickness of the container at various selected locations thereon, the mold comprises several capacitive sensors positioned at various respective locations in the wall defining the molding cavity.

The measurements according to the invention find a particularly advantageous, although not exclusive, application in molds of the hinged mold type comprising at least two half-molds that can be parted from one another by rotation about an axis of rotation about a common axis, which are commonly used in the Applicant Company's machines.

In this case, it is possible to contrive for each half-mold to be provided with at least one capacitive sensor, in other words to provide several capacitive sensors distributed across the two half-molds or alternatively for just one half-mold to be provided with at least one capacitive sensor, in other words the capacitive sensor or sensors would all be grouped together into just one of the half-molds in order to simplify mold design. Provision may also be made for the mold also to comprise a mold bottom distinct from the half-molds and for the mold bottom to be provided with at least one capacitive sensor.

It is further possible to contrive for the mold to be arranged in such a way that the wires connecting the capacitive sensor are engaged in a cut made in the external face of the mold and leave the mold at the lower part or at the upper part thereof. This embodiment proves particularly advantageous when the mold consists of an assembly of several constituent parts, particularly when the molding cavity is made in shells (in which the sensors are inserted) assembled with shell holders themselves supported in mold holders or when the half-molds are supported in mold holders so as not to mechanically weaken the shell holders and/or the mold holders respectively with one or more drillings for the passage of the connecting wires.

Distributors of products packaged in containers, particularly bottles, made of thermoplastic are very keen to have containers the external surface of which is smooth and of impeccable appearance without any visible marks or roughness. It is therefore necessary for the presence of one or more capacitive sensors in the mold to lead to no surface defects in the finished container. To achieve this, according to a third of its aspects, the invention proposes a method of manufacturing a mold as set out hereinabove, which method is characterized in that it comprises the following steps:

a rough form of the molding cavity is machined in the mold, a capacitive sensor is placed in a bore made in the wall of the mold substantially transversely with respect to the final surface of the molding cavity and it is secured therein in its mounted position in such a way that the front face of the capacitive sensor protrudes inward beyond the final surface of the molding cavity, and the machining of the molding cavity is completed, at the same time machining the capacitive sensor in such a way that the front face thereof lies flush with the surface of the molding cavity and is shaped as a continuation of the shape of said surface.

By virtue of this mold manufacturing process, it becomes possible to incorporate the front face of the capacitive sensor in a perfect continuation of the shape of the surface of the molding cavity in such a way that no significant trace is visible on the finished container. Of course, implementation of the method which has just been described entails that the terminal part of the sensor near its front face be hard enough that it can be machined consistently with the surface of the molding cavity.

Finally, according to a fourth of its aspects, the invention proposes a molding installation for manufacturing containers, particularly bottles, by blow-molding or stretch-blow-molding parisons made of thermoplastic, particularly of PET, in a mold comprising at least one molding cavity, which installation, being arranged in accordance with the invention for implementing the measurement method mentioned above, is characterized in that it comprises:

at least one mold arranged in accordance with the invention as indicated above and comprising at least one capacitive sensor inserted in the wall of said mold defining a molding cavity, the front face of the capacitive sensor lying flush with the surface of the cavity and being shaped as a continuation of the shape of said surface, and processing means for processing the signal from the sensor and deducing therefrom information representative of a characteristic of the container.

The detection employed in the context of the invention is based on the perturbation of the electrostatic field on the front face of the sensor when this front face is brought into the presence of an insulating body (the material of the wall of the container) that has a dielectric constant different than that of the air (absence of container wall in contact with it), which perturbation is representative of the characteristic that is to be determined.

Thanks to these provisions, detection is performed on each container as it has just been molded, at the moment when, under the action of the pressurized blowing air, its wall is pressed firmly against the surface of the molding cavity. This detection requires no special manipulation and no special mechanism and takes place automatically as the electrostatic field at the surface of the sensor is modified by the presence of the wall of the container.

Advantageously, the installation may comprise means for displaying the detected value of the characteristic of the container facing the capacitive sensor so as to alert an operator monitoring the operation of the installation.

However, it is preferable, possibly in combination with the preceding measure, to contrive for the installation to comprise means for storing the detected value of the characteristic of the container facing the sensor; then, advantageously, the storage means may be able to store a predetermined number of values detected by the capacitive sensor in respect of containers manufactured in succession and means for analyzing this predetermined number of detected values are provided, these means being able to determine a variation over time of the detected values representative of a variation over time of the characteristic of the containers manufactured in succession: such an arrangement makes it possible to get around individual or very short-term variations and to retain only confirmed variations that are due to a drift in the operating conditions of the installation and liable to affect a great many containers.

In particular then, it is possible to contrive for the analysis means to be connected to an automatic controller managing the operating parameters of the mold in such a way that said operating parameters are modified on the basis of the detected variation in the characteristic. Operation of the installation is thus automated and the appropriate corrections are made without any need to shut down the installation or even to employ operator intervention.

Advantageously, it is possible to contrive for the installation to be equipped with at least one mold provided with several capacitive sensors positioned at various respective locations on the wall defining the molding cavity. It is then possible to check the characteristic at various locations on each container, for example on the shoulder or on the body near the shoulder, on the body (possibly at several locations distant from one another), on the bottom or on the body near the bottom.

The provisions of the invention may find a particularly advantageous application in a rotary molding installation of the rotary carousel type comprising several molds arranged at the periphery: in this case, it is desirable for at least one mold to be equipped with at least one capacitive sensor.

The presence of at least one mold equipped according to the invention allows sampling to be performed with a view to taking corrective action; when all the molds are so equipped it then becomes possible, aside from performing corrective actions, to separate compliant containers from non-compliant containers as appropriate.

In a preferred application of the provisions of the invention, the characteristic measured using at least one capacitive sensor is the wall thickness of the container facing the capacitive sensor.

BRIEF DESCRIPTION OF THE DRAWINGS

The invention will be better understood from reading the detailed description which follows of certain preferred embodiments which are given purely by way of illustration. In this description, reference is made to the attached drawings in which.

DETAILED OF THE INVENTION

Figure 1A:
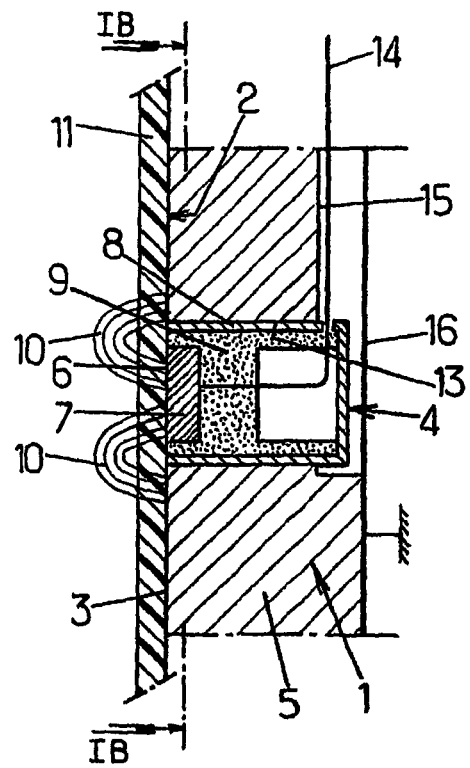
FIG. 1A is a schematic sectioned side view of part of a mold illustrating the arrangements according to the invention.
Figure 1B:
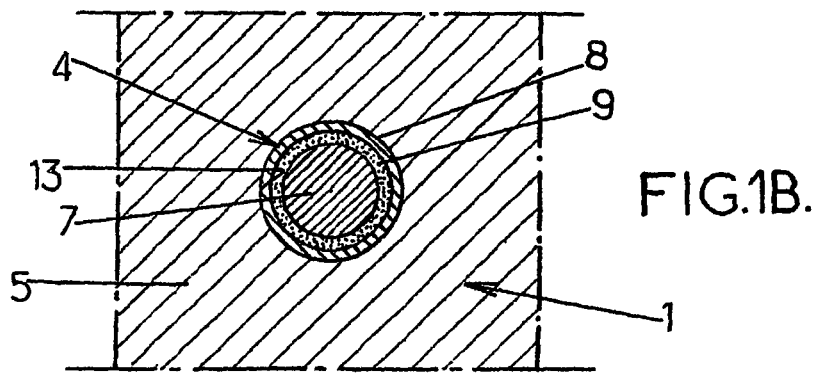
FIG. 1B is a schematic view in section on the line IB-IB of FIG. 1A.

Reference is made first of all to FIGS. 1A and 1B which depict part of a mold 1 with a molding cavity 2 defined by a molding surface 3 for the manufacture of containers, particularly bottles, from parisons (preforms or intermediate containers) made of thermoplastic such as PET.

As is clearly visible in FIG. 1A, there is provided, according to the invention, at least one capacitive sensor 4 inserted in the wall 5 of the mold bordering the molding cavity 2, this capacitive sensor 4 having a front face 6 lying flush with the molding surface 3 of the cavity and shaped as a continuation of the shape of said surface 3.

On the front face 6 of the capacitive sensor 4 there are a central electrode 7 and an external electrode 8 which are separated by an annular intermediate region 9 made of dielectric material, said external electrode 8 being in electrically conducting contact with the mold 1 that forms the electrical ground, as visible in FIG. 1A; in practice, as shown in FIG. 1B, the external electrode 8 is in the form of a metal casing surrounding a mass of dielectric material in which the central electrode 7 is embedded and which is placed directly in contact with the mold.

When the central electrode 7 has voltage applied to it the electrostatic field, depicted diagrammatically as 10, which is formed between the electrodes 7 and 8 at the front face 6 of the sensor is perturbed by the intrusion of a body made of insulating material such as the wall 11 of a container which has just been blown and which therefore presses against the molding surface 3 of the molding cavity 2 and the front face 6 of the capacitive sensor 4. The perturbation introduced by the presence of the wall 11 is dependent on a physical characteristic of this wall 11. The output signal from the capacitive sensor 4 therefore carries information representative of this characteristic which may in particular be the density of the material of which the wall facing the sensor is made (which density is representative of the degree of crystallinity of the material) or alternatively still the thickness of the wall facing the sensor. In the remainder of the description, reference will be made more particularly to the determining of this thickness, it being understood that the provisions of the invention are not restricted to this single application.

Figure 2:
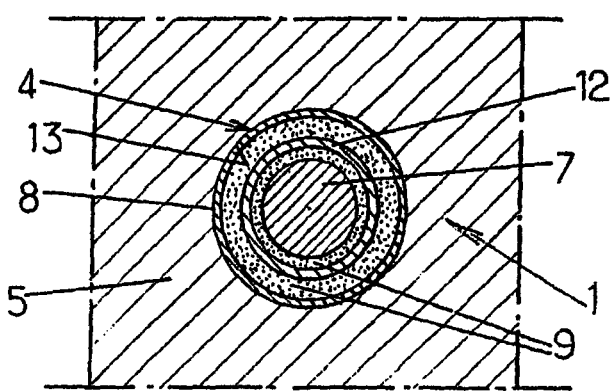
FIG. 2 is a schematic view similar to that of FIG. 1B showing an advantageous alternative form.

The output signal from the capacitive sensor 4 is generally very weak so it is advantageous, in an alternative form, to arrange the capacitive sensor 4 as illustrated in FIG. 2 with a further intermediate electrode 12 (or field electrode) interposed between the central electrode 7 and the external electrode 8.

As can be clearly seen in FIG. 1A, in order for the capacitive sensor 4 to be employed in the best performance conditions, the capacitive sensor 4 is housed and secured in a bore 13 in the wall 5 of the mold 1 which runs approximately perpendicular to the molding surface 3 of the molding cavity 2 when this surface is flat (the case illustrated in FIG. 1A) or to the plane tangential to the molding surface 3 of the molding cavity 2 when this surface is curved.

It is desirable, as shown in FIG. 1A, for the wires 14 connecting the capacitive sensor 4 to be engaged in a cut 15 made in the external face 16 of the wall 5 of the mold and to leave the mold at the lower part or the upper part thereof. Thus, the measures according to the invention can be implemented even in the case of molds of composite structure, for example in the case of molds formed of two molding shells fixed to two respective shell holders, themselves perhaps supported by two respective mold holders without there being any need to hole the shell holder, and any mold holder there might be: thus the risk of weakening that the presence of the bore in the shell holder and possibly the mold holder could carry is set aside.

Figure 3:
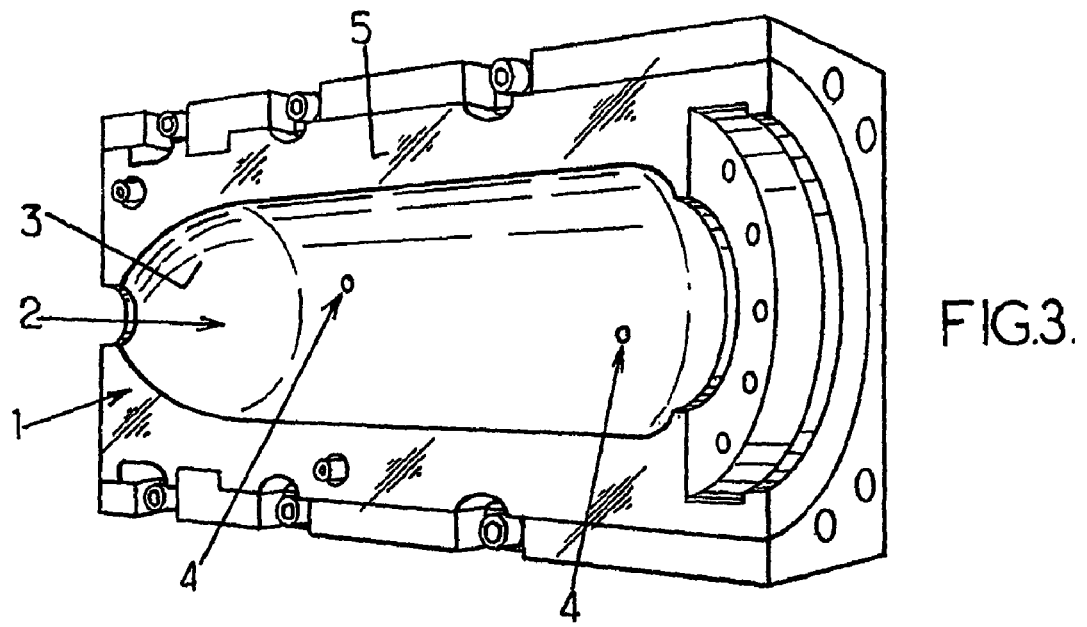
FIG. 3 is a perspective view of a half-mold showing the molding cavity equipped with capacitive sensors according to the invention.

In practice, it might be possible to install in a mold several capacitive sensors 4 arranged at various respective locations on the wall 5 defining the molding cavity 2, as shown in FIG. 3. In particular, it may be advantageous to position sensors at certain key locations on the molding cavity 2, such as in the shoulder or the body in close proximity to the shoulder, in the body at one or more locations (the case illustrated in the example of FIG. 3 in which a half-mold is shown), in the bottom or in the body in close proximity to the bottom.

The arrangements according to the invention may find an application in any kind of mold. However, they must quite particularly find an application in molds of the hinged type which these days are in widespread use and comprise at least two half-molds that can be separated from one another by rotation about an axis of rotation about a common axis (it is a half-mold for this kind of hinged mold which is depicted in FIG. 3). In this case, provision may be made for each half-mold to be provided with at least one capacitive sensor or alternatively for just one half-mold to be provided with at least one capacitive sensor in order in particular to simplify the wiring.

It is particularly important to ensure that the presence of the capacitive sensor 4 flush with the molding surface 3 of the molding cavity 2 does not give rise to any appreciably visible marks on the external surface of the wall of the finished container and for this purpose it is necessary to make sure that the front face of the capacitive sensor 4 is perfectly flush and shaped in perfect continuity with the shape of the molding surface 3 of the molding cavity 2. Hence the invention provides a method for achieving this perfect flush fit, which method is set out hereinbelow with reference to FIGS. 4A to 4D which show part of a mold in diametral section.

Figure 4A:
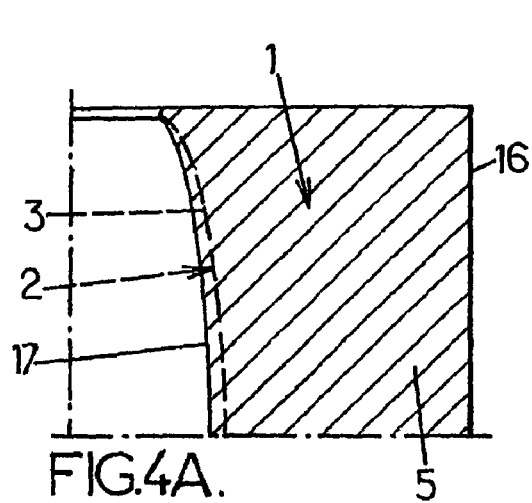
FIGS. 4A to 4D are schematic depictions illustrating steps in a method of manufacturing a mold arranged according to the invention.

To begin with, as shown in FIG. 4A, a rough form 17 of the molding cavity is machined in the wall 5 of the mold 1 using any appropriate technique (the final molding surface 3 of the molding cavity 2 is shown in dashed line).

Figure 4B:
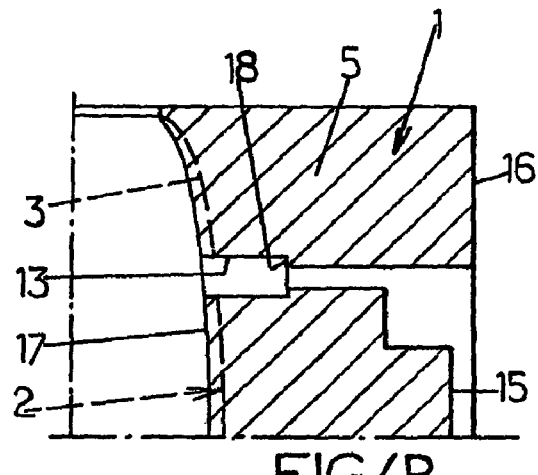

Next, as shown in FIG. 4B, it is possible at this stage (if such a step has not been performed beforehand, for example before machining the rough form of the cavity) to machine a bore 13 through the wall 5 of the mold, which bore 13 runs substantially radially to the final molding surface 3 of the molding cavity 2; for preference, the bore 13 has an axial step 18.

Figure 4C:
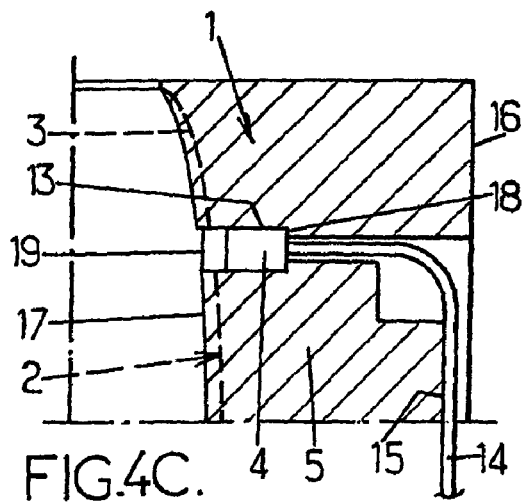

Next, a capacitive sensor 4 is positioned in this bore 13 in axial abutment against the step 18 and is secured therein in its mounted position in such a way that the front face 19 of the capacitive sensor 4 projects inwardly beyond the final molding surface 3 of the molding cavity 2, as shown in FIG. 4C.

Figure 4D:
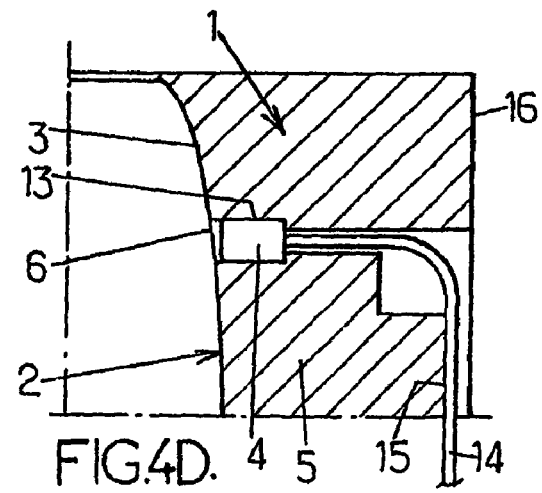

Finally, the machining of the molding cavity 2 is completed by simultaneously machining the capacitive sensor 4 in such a way that the front face 6 thereof lies flush with the molding surface 3 of the molding cavity 2 and is shaped as a continuation of the shape of said surface 3 as shown in FIG. 4D.

Figure 5:
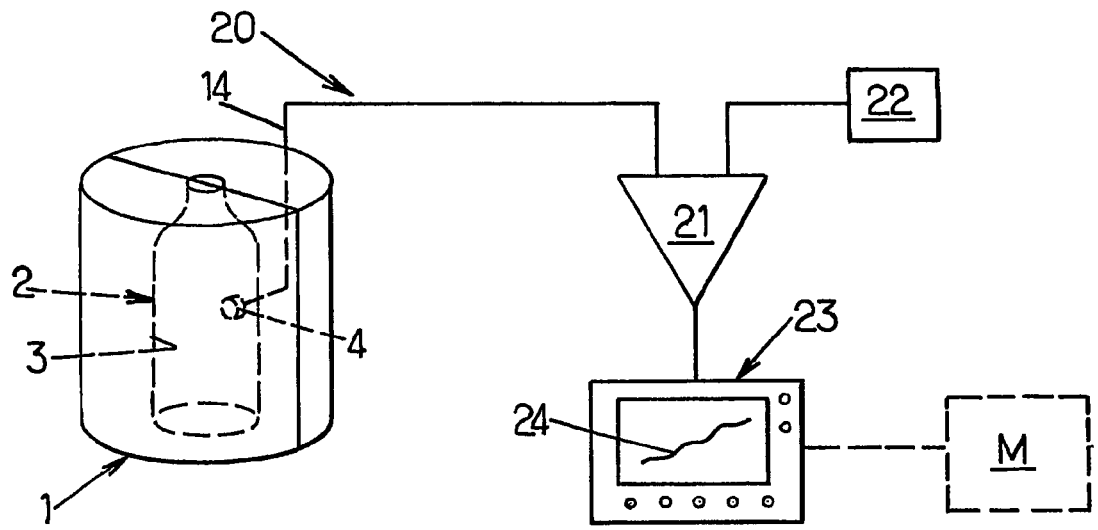
FIG. 5 is a diagram illustrating the construction of an installation for manufacturing molding containers arranged according to the invention.

FIG. 5 schematically illustrates a molding installation denoted in its entirety by the numerical reference 20 for manufacturing containers, particularly bottles, by blow-molding or stretch-blow-molding of parisons made of thermoplastic, particularly PET, in a mold 1 comprising a molding cavity 2, which molding installation is equipped with at least one capacitive sensor 4 under conditions indicated above, that is to say that the capacitive sensor 4 is inserted in the wall 5 of the mold 1, the front face 6 of the sensor lying flush with the molding surface 3 of the molding cavity 2 and being shaped as a continuation of the shape of said surface 3. Signal processing means 23 process the output signal from the capacitive sensor 4 and deliver information representative of the detected value of the thickness of the wall 11 of the container facing the capacitive sensor 4.

It is possible, as illustrated in FIG. 5, to call upon comparison means 21 which receive the output signal from the capacitive sensor 4 and compare its value with a reference value stored in a memory 22, the comparison signal then being delivered to said signal processing means 23.

The signal processing means 23 for processing the output signal from the comparison means 21 may in particular comprise, as shown in FIG. 5, means 24 for displaying the detected value of the thickness of the wall 11 of the container facing the capacitive sensor 4 and/or they may comprise means (M) for storing the detected value of the thickness of the wall 11 of the container. In particular it is then possible to anticipate for the storage means (M) to be capable of storing a predetermined number of values detected by the capacitive sensor in respect of containers manufactured in succession and in that analysis means be provided for analyzing this predetermined number of detected values which means are able to determine a variation over time in the detected values representative of a variation over time in the thickness of the containers manufactured in succession: this processing procedure makes it possible to get around isolated variations that affect just one container or a small number of containers with no lasting effect.

Figure 6:
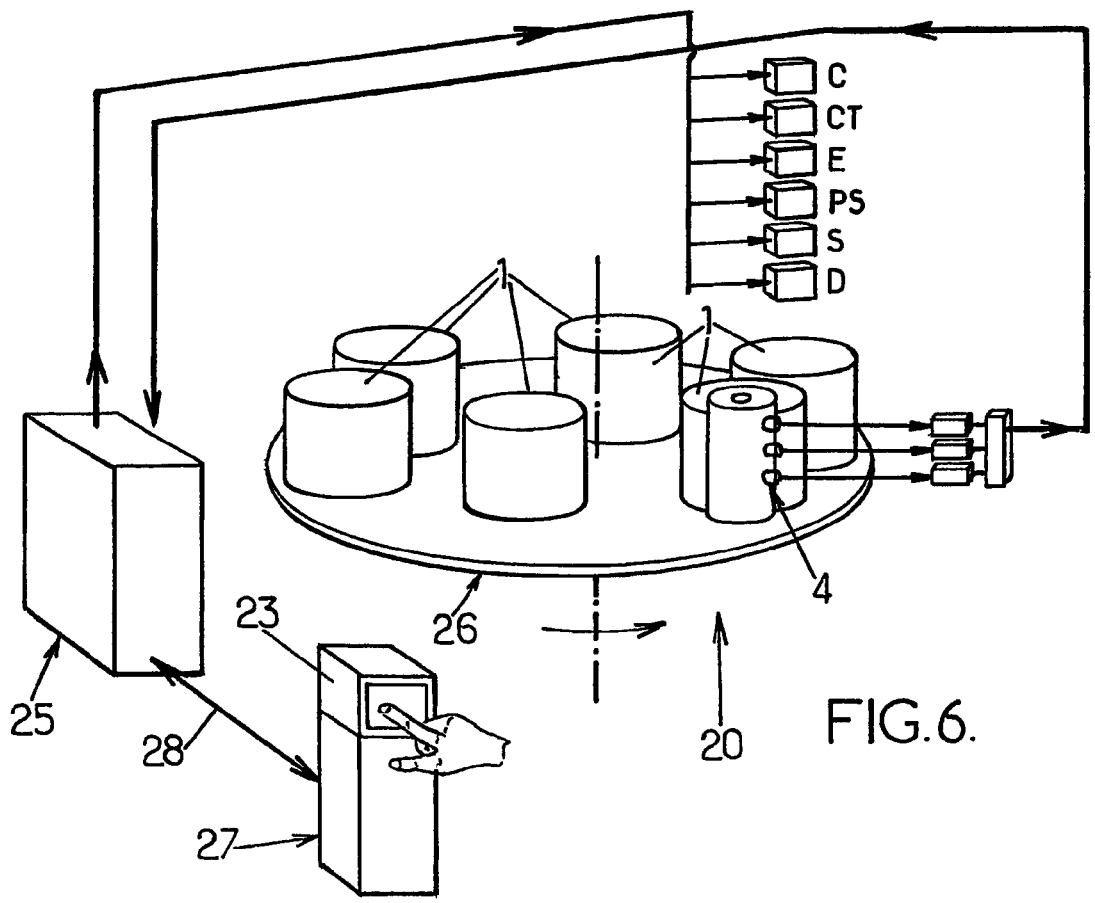
FIG. 6 is a schematic depiction of a preferred embodiment of an installation for manufacturing containers arranged according to the invention.

In this case, it is advantageously possible, as shown in FIG. 6 which schematically illustrates another molding installation, denoted in its entirety by the numerical reference 20, to contrive for these aforementioned signal processing means 23 and/or the aforementioned analysis means to be connected to an automatic controller 25 managing the operating parameters of the mold 1 in such a way that said operating parameters are modified according to the detected variation over time (operating parameters may, nonlimitingly and not necessarily systematically include, for example, the pressure compensation means C associated with the mold, control of the blowing nozzle CT, control of the stretching rod E in the (frequent) event that molding is performed using a stretch-blow-molding process, the pre-blowing control PS, the blowing control S, the degassing or exhaust control D, the preform heating parameters, etc).

As mentioned above, several capacitive sensors may be provided, arranged at various respective locations on the wall 5 defining the molding cavity 2 in a mold 1. In this case, the automatic controller selectively takes account of all the information from these respective capacitive sensors and manages the operation of the mold selectively in the various parts thereof.

The measures according to the invention find a preferred although not exclusive application in the case of a rotary molding installation 20 of the rotary carousel type 26 illustrated in FIG. 6 and comprising several molds 1 arranged at the periphery, which installation is then arranged as mentioned above with at least one mold 1 equipped with at least one capacitive sensor 4 (three sensors are depicted in FIG. 6). Depending on the data processing capacity and/or on the acceptable complexity of the installation (upon which complexity cost is dependent), just one mold 1 may be equipped with a capacitive sensor or with a set of capacitive sensors (it is then assumed that the operation of this mold, which is then used for sampling, is representative of the operation of all the molds in the installation), or alternatively each mold may be equipped with a sensor or with a set of capacitive sensors (the operation of each mold then being managed in isolation). In the example illustrated in FIG. 6, the automatic controller 25 is depicted connected by a data transmission bus 28 to a central control unit (PCC) 27 which may then for example include the comparison means 21 and memory means 22 containing the reference value as mentioned above, together with the signal processing means 23 and the display means 24.

The invention claimed is:

1. A method for measuring at least one physical characteristic of containers manufactured by blow-molding or stretch-blow-molding of parisons made of thermoplastic, in a mold comprising at least one molding cavity, wherein said measurement is made by detecting a capacitive effect or a variation in capacitive effect in the mold during blow-molding or stretch-blow-molding.

2. The method as claimed in claim 1, wherein the measured characteristic is the wall thickness of the container at least at one location thereon.

3. The method as claimed in claim 1, wherein the measured characteristic is the density of the material of the wall of the container at least at one location thereon.

4. The method as claimed in claim 1, wherein the measurement is made between the end of blow-molding or stretch-blow-molding and the start of mold opening while the wall of the container is in close contact with the molding surface of the molding cavity.

5. The method as claimed in claim 1, wherein the thermoplastic is PET.

6. A mold for the manufacture of containers by blow-molding or stretch-blow-molding of parisons made of thermoplastic, the mold comprising at least one molding cavity wherein, in order to measure at least one physical characteristic of the containers by detecting a capacitive effect or a variation in capacitive effect in the mold during blow-molding or stretch-blow-molding, said mold further comprises at least one capacitive sensor inserted in a wall of the mold defining the molding cavity, the front face of the capacitive sensor lying flush with the molding surface of the molding cavity and being shaped as a continuation of the shape of said surface.

7. The mold as claimed in claim 6, wherein said capacitive sensor comprises a front face on which there are a central electrode and an external electrode which are separated by an annular intermediate region of dielectric material, said external electrode being in electrically conducting contact with the mold which forms the electrical ground.

8. The mold as claimed in claim 6, wherein said capacitive sensor further comprises an intermediate electrode, which is a field electrode, interposed between the central electrode and the external electrode.

9. The mold as claimed in claim 8, wherein said intermediate electrode is connected in such a way as to be at a different potential than the central and external electrodes between which it the intermediate electrode is interposed.

10. The mold as claimed in claim 6, wherein said capacitive sensor is housed and fixed in a bore in the wall of the mold which runs approximately perpendicular to the molding surface of the molding cavity when this surface is flat or to the plane tangential to the molding surface of the molding cavity when this surface is curved.

11. The mold as claimed in claim 6, comprising several capacitive sensors positioned at various respective locations in the wall defining the molding cavity.

12. The mold as claimed in claim 6, being of the hinged mold type comprising at least two half-molds that can be parted from one another by rotation about an axis of rotation about a common axis.

13. The mold as claimed in claim 12, wherein each half-mold is provided with at least one capacitive sensor.

14. The mold as claimed in claim 12, wherein only one half-mold is provided with at least one capacitive sensor.

15. The mold as claimed in claim 12, further comprising a mold bottom distinct from the half-molds and in that the mold bottom is provided with at least one capacitive sensor.

16. The mold as claimed in claim 6, wherein wires connecting said capacitive sensor are engaged in a cut made in the external face of the mold and leave the mold at the lower part or at the upper part thereof.

17. The mold as claimed in claim 6, wherein the thermoplastic is PET.

18. A method of manufacturing a mold, the mold configured for the manufacture of containers by blow-molding or stretch-blow-molding of parisons made of thermoplastic, the mold including at least one molding cavity wherein, in order to measure at least one physical characteristic of the containers by detecting a capacitive effect or a variation in capacitive effect in the mold during blow-molding or stretch-blow-molding, the mold includes at least one capacitive sensor inserted in a wall of the mold defining the molding cavity, the front face of the capacitive sensor lying flush with the molding surface of the molding cavity and being shaped as a continuation of the shape of said surface; the method comprising the following steps:

a rough form of the molding cavity is machined in the mold, the at least one capacitive sensor is placed in a bore made in the wall of the mold substantially transversely with respect to the final molding surface of the molding cavity and the capacitive sensor is secured therein in its a mounted position in such a way that the front face of the capacitive sensor protrudes inward beyond the final molding surface of the molding cavity, and the machining of the molding cavity is completed, at the same time machining the capacitive sensor in such a way that the terminal front face thereof lies flush with the molding surface of the molding cavity and is shaped as a continuation of the shape of said surface.

19. A molding installation for manufacturing containers, by blow-molding or stretch-blow-molding parisons made of thermoplastic, in a mold comprising at least one molding cavity, said installation comprising, in order to measure at least one physical characteristic of the containers by detecting a capacitive effect or a variation in capacitive effect in the mold during blow-molding or stretch-blow-molding:

at least one mold comprising the at least one mold cavity and at least one capacitive sensor inserted in the wall of said mold defining the molding cavity, the front face of the capacitive sensor lying flush with the molding surface of the molding cavity and being shaped as a continuation of the shape of said surface, and processing means for processing the signal from the capacitive sensor and deducing therefrom information representative of a characteristic of the container.

20. The installation as claimed in claim 19, comprising means for displaying the detected value of the characteristic of the container facing the capacitive sensor.

21. The installation as claimed in claim 19, comprising means for storing the detected value of the characteristic of the container facing the capacitive sensor.

22. The installation as claimed in claim 21, said storage means are able to store a predetermined number of values detected by the capacitive sensor in respect of containers manufactured in succession and wherein analysis means for analyzing this predetermined number of detected values are provided, these analysis means being able to determine a variation over time of the detected values representative of a variation over time of the characteristic of the containers manufactured in succession.

23. The installation as claimed in claim 22, wherein said analysis means are connected to an automatic controller managing the operating parameters of the installation in such a way that said operating parameters are modified on the basis of the detected variation in the characteristic.

24. The installation as claimed in claim 19, several capacitive sensors are positioned at various respective locations on the wall defining the molding cavity.

25. The installation as claimed in claim 19, wherein the thermoplastic is PET.

26. The installation as claimed in claim 19, wherein the characteristic measured using at least one capacitive sensor is the wall thickness of the container facing the capacitive sensor.

27. A rotary molding installation of the rotary carousel type comprising several molds arranged around the periphery, the molding installation configured for the manufacture of containers by blow-molding or stretch-blow-molding parisons made of thermoplastic, the molds each comprising at least one molding cavity, the installation comprising, in order to measure at least one physical characteristic of the containers by detecting a capacitive effect or a variation in capacitive effect in the molds during blow-molding or stretch-blow-molding:

the at least one capacitive sensor inserted in the wall of at least one of the molds, the wall defining the molding cavity, the front face of the capacitive sensor lying flush with the molding surface of the molding cavity and being shaped as a continuation of the shape of said surface, and processing means for processing the signal from the capacitive sensor and deducing therefrom information representative of a characteristic of the container.

* * * * *